United States Patent [19]

Kramer

[11] Patent Number: 4,881,548

[45] Date of Patent: Nov. 21, 1989

[54] TANNING BED TOP COVER ACTUATOR

[75] Inventor: Donald D. Kramer, Yakima, Wash.

[73] Assignee: Circle K Enterprises, Inc., Yakima, Wash.

[21] Appl. No.: 12,844

[22] Filed: Feb. 10, 1987

[51] Int. Cl.[4] ............................................. A61N 5/06
[52] U.S. Cl. .................................. 128/376; 128/396; 254/278
[58] Field of Search ............... 128/373, 374, 378, 395, 128/396, 376; 5/414, 416, 63, 83, 88; 272/117, 123; 254/266, 277, 276, 278; 248/610, 138 R; 294/1.1, 82.16; 318/777, 778

[56] References Cited

U.S. PATENT DOCUMENTS

| | | | |
|---|---|---|---|
| 2,603,851 | 7/1952 | Hawkins | 5/88 |
| 4,145,645 | 3/1979 | Price et al. | 318/777 |
| 4,168,793 | 9/1979 | Knight | 5/88 |
| 4,202,064 | 5/1980 | Joergensen | 5/88 |
| 4,335,714 | 6/1982 | Frei et al. | 128/373 |
| 4,361,312 | 11/1982 | Schreyer et al. | 254/276 |
| 4,471,956 | 9/1984 | Marlo | 272/117 |
| 4,600,009 | 7/1986 | Kramer et al. | 128/376 |

FOREIGN PATENT DOCUMENTS

| | | | |
|---|---|---|---|
| 3303795 | 8/1984 | Fed. Rep. of Germany | 128/395 |
| 20536 | of 1905 | United Kingdom | 128/373 |
| 917372 | 2/1963 | United Kingdom | 5/88 |

*Primary Examiner*—Edward M. Coven
*Assistant Examiner*—Mark S. Graham
*Attorney, Agent, or Firm*—Seed and Berry

[57] ABSTRACT

A support for a top cover for a tanning bed using three redundant straps spaced such that any two of the three will support the cover in the event of a failure of one of the other straps. Controls are provided for electrically controlling the operation of the motor for the top cover. These controls have the ability to raise the top cover automatically after a certain time delay or only after a certain sequence of manual actuation to provide improved control of the operation of the power top cover.

7 Claims, 2 Drawing Sheets

TANNING BED TOP COVER ACTUATOR

TECHNICAL FIELD

This invention relates to support systems and controls for manipulating the heavy top cover of a tanning bed relative to the lower unit of the tanning bed.

BACKGROUND ART

Tanning beds are large structures having a lower unit which houses a plurality of ultraviolet lights. The lower unit is relatively stationary and supports the weight of the operator who is being tanned. A movable top cover, which also houses a plurality of ultraviolet lights, is supported above the lower unit and must be raised to allow access by the operator and lowered to bring the ultraviolet lights of the top cover into close proximity to the operator.

There are various arrangements for supporting the top cover and raising and lowering the top cover relative to the lower unit. An earlier unit employed torsion springs for supporting the weight of the top unit. The operator raised and lowered the top unit manually with assistance from the torsion springs.

The top cover of the tanning bed is quite heavy. While providing an assisting force, such as torsion springs, to enable the operator to manually raise and lower the top cover, it is believed more desirable to make the raising and lowering completely electrically powered. However, electrically powered top cover raising devices desirably should exhibit several qualitites. First, loss of power should not allow the top cover to fall against the lower unit, possibly injuring the operator. Second, the operator should be able to move the top cover sufficiently to exit the lower unit in the event of a loss of power. Third, the supports which carry the weight of the top cover should be redundant, such that if one support fails, there is at least one other which will not only support the top cover but prevent it from tilting substantially so that it may not come in contact with the lower unit.

DISCLOSURE OF THE INVENTION

It is an object of the invention to provide a support for a top cover of a tanning bed which is powered and supported by members, the failure of any one of which will not allow the top cover to fall into contact with the lower unit of the tanning bed.

It is another object of the invention to provide a top cover that is flexibly supported by at least three straps which are adjustable to maintain alignment of the top cover over the lower unit of the tanning bed.

It is still another object of the invention to provide controls for electrically controlling the operation of the motor for the top cover of a tanning bed, the controls having features that operate the motor to raise the top cover automatically after a certain time delay or only after a certain manual actuation to provide improved control of the operation of the powered top cover.

Basically, these objects are obtained by mounting the top cover from the frame of the tanning bed with a plurality of straps spaced lengthwise along the top cover. The straps are driven by a common axle and can be retracted and extended simultaneously by a motor powering the axle. Any one of the three straps can fail and the top cover will still be supported by the remaining two straps without substantial tilting of the cover. The straps are adjustable relative to the top cover for maintaining alignment of the top cover relative to the lower unit.

In a preferred embodiment, the controls are provided to discourage the operator from frequently manually operating the "raise" button. This control requires the manual "raise" button be actuated for a period of approximately five seconds before the motor is energized to raise the top unit. Another control is provided by which the cover is automatically raised after a predetermined time interval. This raises the top cover automatically should the operator fall asleep during a tanning cycle.

The flexible supports advantageously allow the top cover to be swung horizontally clear of the lower unit should there be a power failure and the operator wish to exit the tanning unit.

The strap support system is inexpensive to manufacture and safe in its operation. The controls prevent misuse of the powered top cover support system and assure the operator of a comfortable, safe cycle of tanning.

BEST MODE FOR CARRYING OUT THE INVENTION

Figure 1:
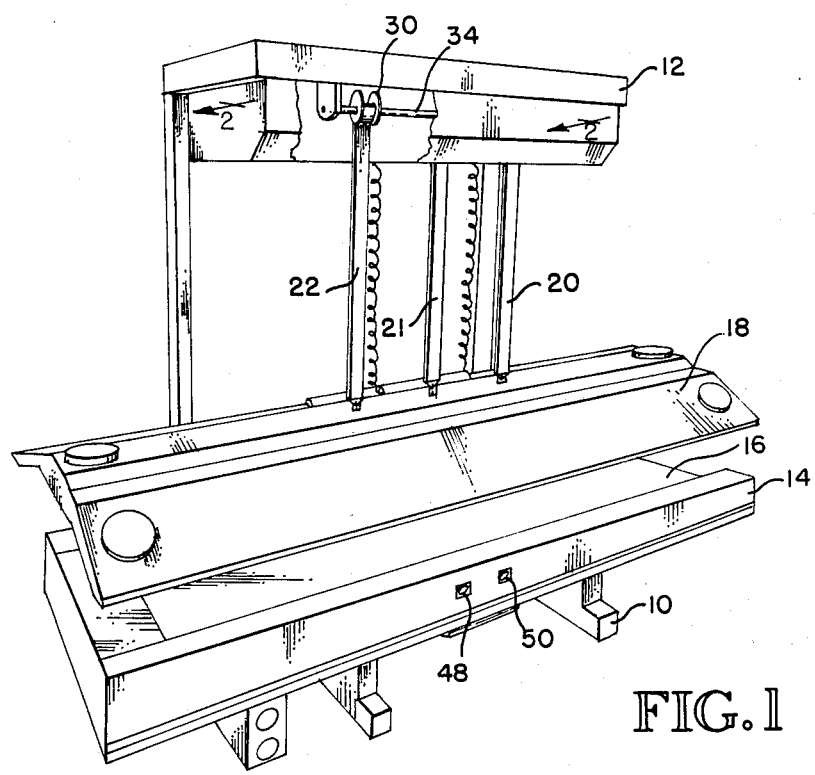
FIG. 1 is a perspective of a tanning bed embodying the principles of the invention.

As best shown in FIG. 1, the tanning bed includes a frame 10 having an upper support structure 12. A lower unit 14 is mounted on the frame 10. The lower unit 14, as is well known, contains a plurality of ultraviolet lights generally running the length of the lower unit. A plastic cover 16 rests on the lower unit to support the weight of the operator to be tanned.

Figure 2:
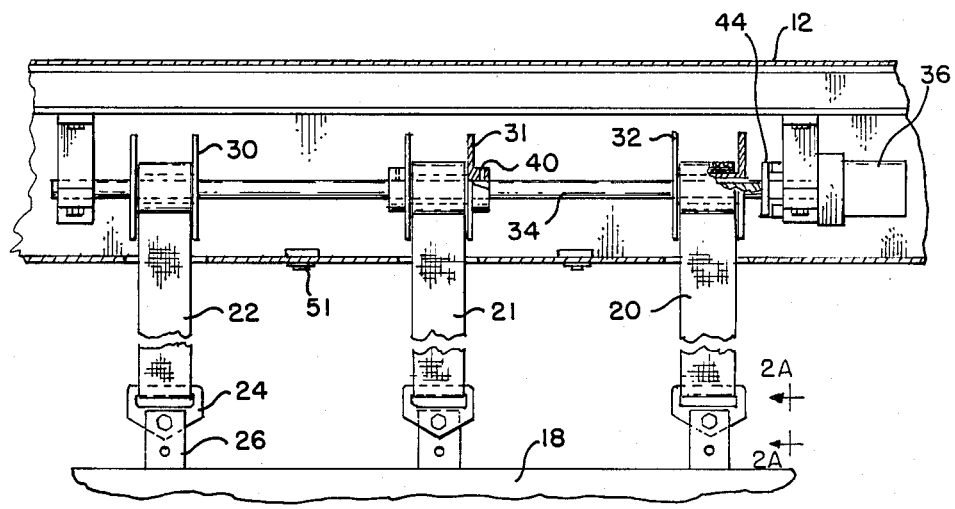
FIG. 2 is a section taken along the lines 2—2 of FIG. 1.
Figure 2A:
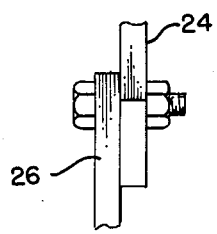
FIG. 2A is a fragmentary detail taken in the direction of arrows 2A—2A of FIG. 2.

A top cover 18 is supported above the lower unit and is raised and lowered by a plurality of straps 20, 21 and 22. The straps are connected at their lower ends by connecting plates 24 that are bolted to upright brackets 26 on the top cover. The brackets 26 are provided with vertically spaced holes to allow the straps to be connected at different distances relative to the top cover. Furthermore, as is best shown in FIG. 2A, the connecting plates 24 can be placed on the fore or aft side of the brackets 26 for aligning the top cover relative to the lower unit in a horizontal direction.

The straps are made of non-stretchable nylon and are fixed at their upper ends to reels 30, 31 and 32 that are connected to a common axle 34. The axle 34 is mounted in bearings and driven by a motor 36 via a 60:1 reduction drive. The reduction drive prevents the cover from lowering by turning the motor when the motor is deenergized.

The reels 30 and 32 are keyed to the axle. The length of the straps 20 and 22 is fixed such that upon loss of electrical power, the cover can move toward the lower unit no further than the full length of the straps. This feature assures that power failure will not result in the top cover striking the operator lying in the lower unit.

The center strap is also fixed to its reel 31. Reel 31, however, is connected to the axle 34 by adjustable setscrews 40. The center strap is slightly longer than the end straps. The setscrews 40 allow the reel to be rotated so that only a very slight tension is applied to the center strap when the weight of the top cover is being carried by the end straps 20 and 22. The center strap serves more as a safety strap than a primary lifting strap. Upon breakage of any of the three straps, however, the other two straps are spaced sufficiently lengthwise from one another and are of sufficient strength to carry the full load of the top cover and prevent its tilting substantially end to end.

Should there be a power failure while the operator is using the tanning bed and the top cover is the lowered position, the operator may tilt the bed such that the bed rotates about the flexible straps so that the front edge of the top cover is raised and the lower edge lowered to exit from the front of the tanning unit. In addition, the operator may swing the top cover out of alignment with the lower unit to also exit the lower unit. The adjustments between the bracket 26 and the connecting plate 24 allow the top unit to be aligned horizontally and vertically over the lower unit even though the floor upon which the frame rests may be not perfectly horizontal.

Figure 3:
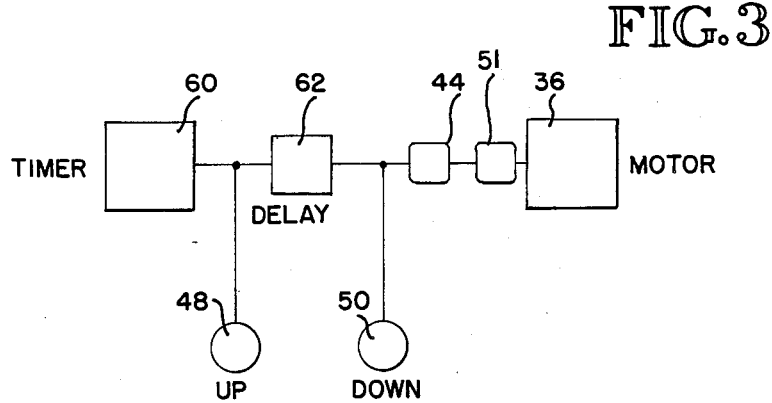
FIG. 3 is a schematic of the controls for operating the top cover motor.

The control system for energizing the motor 36 is best shown in FIG. 3. When the top cover is raised, the motor is automatically de-energized by a conventional rotary switch 44. Similarly, when the top cover is lowered, it is automatically turned off in the lower position by the switch 44. Adjustments in-between can be controlled by manual "raise" and "lower" buttons 48 and 50. Switches 51 also de-energize the motor when the top cover is fully raised if the rotary limit switch 44 becomes inactivated for some reason.

As best shown in FIG. 3, a timer 60 is provided. This timer is actuated by the main control, frequently a coin-operated control which sets a maximum time limit for operation of one tanning cycle. At termination of that tanning cycle plus a few moments' delay, the timer automatically energizes the motor to raise the top cover. This feature is desirable for operators who tend to fall asleep during a tanning cycle. When they awake, the top cover will already be raised for their convenience.

A time delay 62 is preferably also employed. This time delay is connected with the "raise" button 48 to block energization of the motor until approximately five seconds has occurred. This feature discourages the operator from accidentally or intentionally raising the top cover until it is intended that the top cover be raised.

While the preferred embodiments of the invention have been illustrated and described, it should be understood that variations will be apparent to one of ordinary skill. Accordingly, the invention is not to be limited to the specific embodiment shown in the drawings.

I claim:

1. A tanning bed and an apparatus for supporting, raising and lowering a top cover of said tanning bed, comprising:
    a frame having an upper support structure supporting a top member;
    a bottom member on which a user reclines while in said tanning bed, said bottom member having a plurality of ultraviolet lights and being connected to said frame and located directly below said top member;
    a rotatable axle coupled to said frame at an upper region;
    a motor coupled to said axle for rotating said axle to lower or raise said top member;
    a plurality of reels attached to said axle said plurality of reels including a plurality of reels fixedly attached to said axle and a variable position reel;
    a plurality of flexible first support straps coupled to said fixed reels at one end thereof and to said top member at another end thereof, all of said first support straps being the same length;
    a flexible second support strap coupled at one end thereof to said variable position reel means, said variable position reel means capable of being fixed to said axle at a plurality of angular positions and to said top member at another end thereof, said second support strap being of a length longer than said first support straps, said first and second support straps being of such a length that if fully extended from said axle and coupled to said top member, permitting said top member to be in the lowest possible position, said top member is positioned a predetermined distance above said bottom member, said predetermined distance being greater than the expected size of a user's body when said user is reclined on said bottom member; and
    a locking member means for locking said variable position reel means in a desired fixed position on said axle, said second support strap being coupled to said variable position reel.

2. The apparatus of claim 1 wherein said variable position reel means is rotatable with said second support strap coupled between said variable position reel and said top member for taking up slack in said support member and placing said second support member in tension.

3. The apparatus of claim 1, further including a first rotary switch means coupled to said axle and to said motor for turning off said motor when said axle has rotated a predetermined number of times.

4. The apparatus of claim 1, further including a reduction drive coupled between said motor and said axle.

5. The apparatus of claim 1, further including a connecting plate means and a bracket means for connecting each of said flexible straps to said top member; and
    means for adjusting the vertical connection between each of said flexible straps and said top member independent of each other to permit the top member to be aligned vertically and horizontally over said bottom member even though said bottom member is not perfectly horizontal.

6. A tanning bed and an apparatus for supporting, raising and lowering a top cover of a tanning bed, comprising:
    a frame member having an upper support structure supporting a top member;
    a bottom member on which a user reclines while in said tanning bed, said bottom member having a plurality of ultraviolet lights and being connected to said frame and located directly below said top member;
    a rotatable axle coupled to said frame at an upper region:
    a motor coupled to said axle for rotating said axle to lower or raise said top member;
    a plurality of reels attached to said axle;
    a plurality of flexible first support straps coupled to fixed reels at one end thereof and to said top member at another end thereof, all of said first support straps being the same length;

a flexible second support strap coupled to a reel at one end thereof and to said top member at another end thereof, said second support strap being of a length longer than said first support straps, said first and second support straps being of such a length that if fully extended from said axle and coupled to said top member, permitting said top member to be in the lowest possible position, said top member is positioned a predetermined distance above said bottom member, said predetermined distance being greater than the expected size of a user's body when said user is reclined on said bottom member;

a manually actuated "raise" button means for turning on said motor to raise said top member; and a delay circuit means coupled in series with said "raise" button and said motor for requiring that said "raise" button be depressed for a predetermined time prior to turning on said motor to raise said top member.

7. The apparatus of claim 6 wherein said predetermined time is 5 seconds.

* * * * *